US005549596A

United States Patent [19]
Latina

[11] Patent Number: 5,549,596
[45] Date of Patent: Aug. 27, 1996

[54] SELECTIVE LASER TARGETING OF PIGMENTED OCULAR CELLS

[75] Inventor: Mark A. Latina, North Andover, Mass.

[73] Assignee: The General Hospital Corporation, Boston, Mass.

[21] Appl. No.: 545,887

[22] Filed: Oct. 20, 1995

Related U.S. Application Data

[63] Continuation of Ser. No. 88,855, Jul. 7, 1993, abandoned.

[51] Int. Cl.$^6$ .................................................. A61B 17/36
[52] U.S. Cl. ................................................................ 606/4
[58] Field of Search ................................ 606/2, 3, 4, 5, 606/6; 607/88, 89

[56] References Cited

U.S. PATENT DOCUMENTS

| 3,884,236 | 5/1975 | Krasnov | 606/3 |
|---|---|---|---|
| 3,943,931 | 3/1976 | Krasnov | 606/4 |
| 4,391,275 | 7/1983 | Fankhauser et al. | 606/4 |
| 4,461,294 | 7/1984 | Baron | 606/5 |
| 4,538,608 | 9/1985 | L'Esperance, Jr. | 606/10 |
| 4,558,698 | 12/1985 | O'Dell | 606/6 |
| 5,123,902 | 6/1992 | Muller et al. | 606/5 |
| 5,312,395 | 5/1994 | Tan et al. | 606/9 |

FOREIGN PATENT DOCUMENTS 0172490  2/1986  European Pat. Off. .................. 606/9

OTHER PUBLICATIONS

Huis et al., "Localized Surgical Debridement of RPE by O–Switched Neodymiumyag Laser", Arvo Abs., May 1993, p. 959.

Fox et al., "Switched Ruby Laser Irradiation of Melanotic Conjunctiva", Arvo Abs., May 1993, p. 958.

Primary Examiner—Angela D. Sykes
Assistant Examiner—Sonya Harris-Ogugua
Attorney, Agent, or Firm—Fish & Richardson P.C.

[57] ABSTRACT

A method of damaging pigmented intraocular cells, a patient with a disease, which involves selectively damaging pigmented cells in an intraocular area by irradiating the area with laser radiation of radiant exposure between about 0.01 and about 5 Joules/cm$^2$, while sparing nonpigmented cells and collagenous structures within the irradiated area. The method is useful for the treatment of glaucoma, intraocular melanoma, and macular edema.

29 Claims, 6 Drawing Sheets 5,549,596

SELECTIVE LASER TARGETING OF PIGMENTED OCULAR CELLS

This invention was made with Government support under Contract N00014-86-00117 awarded by the Department of the Navy. The Government has certain rights in the invention.

STATEMENT AS TO FEDERALLY SPONSORED RESEARCH

Studies were supported in part by National Eye Institute grant K11 EY00292. The United States government, therefore, has certain rights in this invention.

This application is a continuation of U.S. Ser. No. 08/088,855, filed Jul. 7, 1993, now abandoned.

BACKGROUND OF THE INVENTION

This invention relates to laser-induced damage to pigmented ocular cells.

Laser treatment of tissues within the eye is commonly used to treat diseases such as proliferative diabetic retinopathy, other forms of neovascularization, open-angle glaucoma, cataracts, and intraocular tumors. While laser treatment has greatly enhanced the performance of many types of ocular surgery, certain procedures are adversely affected by the nonselective nature of laser-induced tissue damage. Current ocular surgery lasers cause tissue coagulation or ablation, meaning total removal or vaporization, with no ability to discriminate between cell or tissue types.

For example, two types of ablative laser surgery are now commonly used to treat open-angle glaucoma. Glaucoma refers to abnormally elevated intraocular pressure, and is most commonly caused by increased resistance to outflow of the continuously produced aqueous humor. The aqueous humor exits the eye through the trabecular meshwork (TM) at the periphery of the anterior chamber. The TM consists of collagenous beams and plates, covered with phagocytic TM cells, and enclosing passages through which the aqueous humor flows, finally entering the vasculature via Schlemm's canal. Pathologic changes in the trabecular meshwork are thought to be involved in the etiology of certain forms of glaucoma.

The resistance by the TM is lowered, and intraocular pressure subsequently decreased, by laser surgery to ablate portions of the TM. Laser trabeculoplasty surgery utilizes long pulses (of approximately 100 msec) of laser radiation at high fluency, which is a measure of radiant exposure, or energy per area of tissue ($mJ/cm^2$). This procedure causes immediate tissue coagulation and focal burns of the TM, as well as subsequent scarring in the burned areas. Aqueous flow is thought to be improved in the region adjacent to the lasered tissue. The trabeculoplasty procedure results in lowered intraocular pressure which lasts for only a limited time period. The scar tissue which forms after the procedure severely limits the efficacy of subsequent trabeculoplasties on a given patient. In an alternate procedure, trabeculopuncture, the absorption of laser radiation at high fluence and irradiance ($Watts/cm^2$) causes photodisruption of the TM tissue, producing a hole through the TM into Schlemm's canal, the major outflow vessel. The laser-created trabeculopuncture channel into Schlemm's canal eventually fills in with fibrotic tissue; the beneficial effects of the procedure on intraocular pressure are not permanent.

SUMMARY OF THE INVENTION

The invention features a method of selectively damaging pigmented intraocular cells in a patient with a disease, which involves selecting an intraocular area containing a pigmented cell and a nonpigmented cell, irradiating the area with laser radiation of radiant exposure between about 0.01 and about 5 $Joules/cm^2$, and damaging the pigmented cell without killing the nonpigmented cell.

In a preferred embodiment, the radiation is delivered in pulses with pulse duration of between about 1 nsec and about 2 μsec. The radiation may be delivered in a single pulse. In a further preferred embodiment, the laser radiation impinges upon the intraocular area in a target spot of between about 0.05 and about 1.5 mm in diameter. Preferably, the laser radiation has a wavelength which is more highly absorbed in pigmented than in nonpigmented cells.

The method involves selectively damaging pigmented intraocular cells, such as trabecular meshwork cells, retinal pigmented epithelial cells, uveal pigmented cells, melanoma cells, or conjunctival pigmented cells. The pigmented cells may contain endogenously synthesized pigment, or may be phagocytic cells into which exogenous pigment is introduced by contacting the phagocytic cells with exogenous pigment before irradiating the area containing the cells. Endogenous pigment refers to pigment synthesized and retained within a cell, and exogenous pigment refers to pigment within a cell which was not synthesized within the same cell. In a preferred embodiment, the phagocytic cell is a trabecular meshwork cell and exogenous pigment is introduced into the aqueous humor by laser irradiation of the iris.

In yet another embodiment, the intraocular area is trabecular meshwork, and the laser radiation is delivered via a slit lamp delivery system and is directed into the trabecular meshwork by a goniolens.

In another aspect, the invention features a method of damaging trabecular meshwork cells, involving irradiating a region of trabecular meshwork containing cells and collagen beams with laser radiation characterized by radiant exposure of between about 0.01 and about 5 $Joules/cm^2$, and selectively damaging the trabecular meshwork cells without damaging the collagen beams.

In a further aspect, the invention features a method of damaging conjunctival pigmented epithelial cells in a patient with a disease, involving selecting an area of conjunctiva containing a pigmented cell and a nonpigmented cell, irradiating the area with laser radiation, wherein the radiation has radiant exposure of between about 0.01 and about 5 $Joules/cm^2$ and damaging the pigmented cell without killing the nonpigmented cell. In a preferred embodiment, the radiation is delivered in pulses with pulse duration of between about 1 nsec and about 2 μsec. The disease is intended to include conjunctival melanoma (benign or malignant), pigmented nevus, or other conjunctival diseases of pigmented tissues.

The invention provides a method for selectively damaging pigmented intraocular cells, while nonpigmented cells and structures are not damaged. The method is useful in the treatment of diverse diseases of pigmented tissues within the eye. In a preferred embodiment, the method is useful in treating glaucoma.

Other features and advantages of the invention will be apparent from the following description and from the claims.

DETAILED DESCRIPTION OF EXEMPLARY EMBODIMENTS

Figure 1:
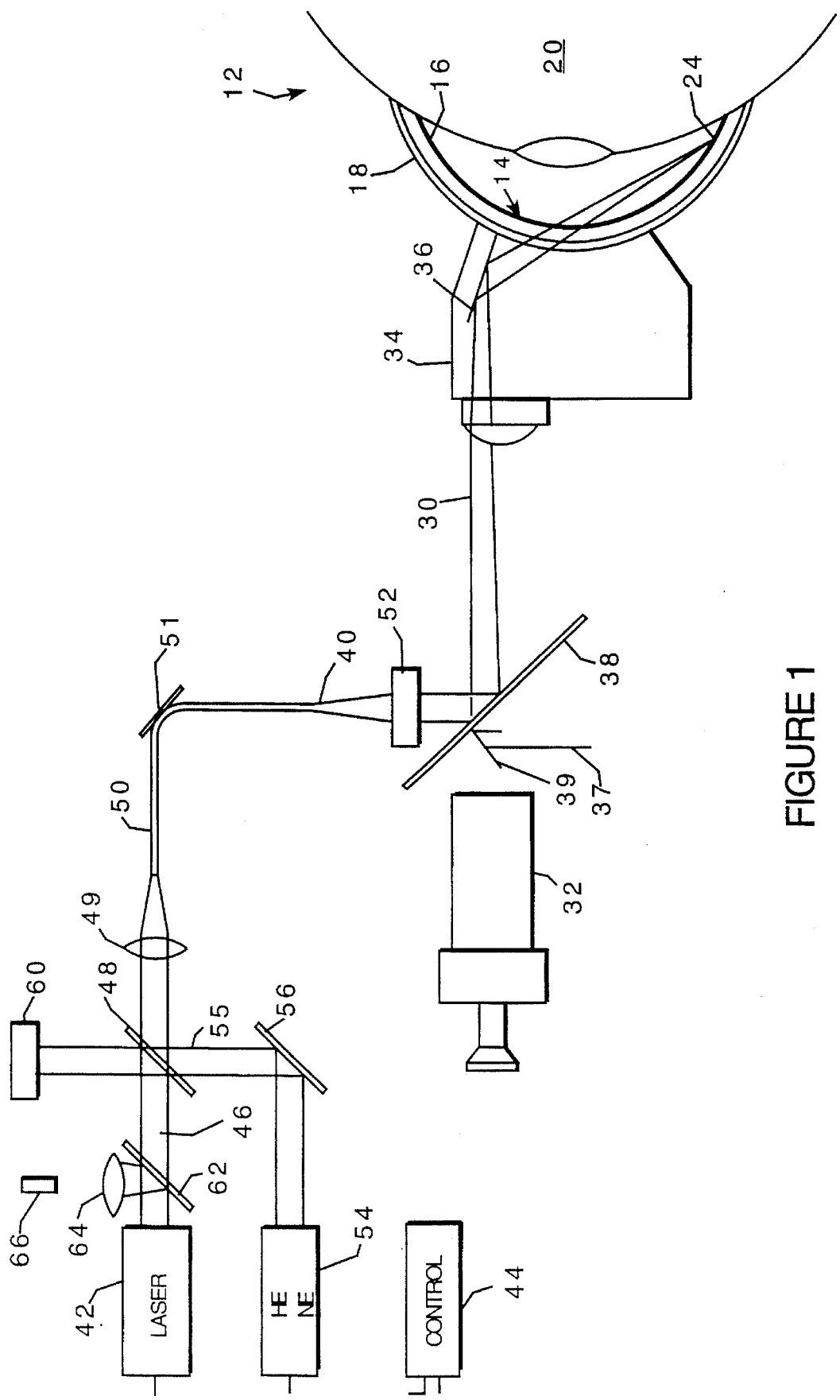
FIG. 1 is a diagram of a laser apparatus for use in practicing the method of the invention.

The method of the present invention involves selectively damaging or killing ocular cells containing pigment, while sparing nonpigmented cells and tissue structures within the region of irradiation.

Briefly, an area of intraocular tissue containing pigmented cells is irradiated with a laser, such as a q-switched Nd:YAG laser. The pigment in the cells makes the pigmented target cells optically denser than the nonpigmented surrounding cells, and thus more susceptible to laser-induced damage at selected laser wavelengths and fluences. In a preferred mode, laser energy at low fluences, impinging on the target tissue areas for short time durations, selectively kills the pigmented target cells with minimal damage to surrounding cells. The selectivity of tissue damage is of great clinical benefit in treating pathological conditions restricted to pigmented cells, including conditions of phagocytic cells which can be induced to take up exogenous pigment. For these conditions, the invention allows killing of affected cells while preserving the integrity of unaffected, nonpigmented cells and support tissues, thereby minimizing adverse effects of the surgery on the residual function of the ocular tissues.

The method of the invention utilizes laser irradiation of low fluence, or radiant exposure. Fluences of about 0.001–5.0 Joules/cm$^2$, and preferably of about 0.01–1.0 Joules/cm$^2$, are found to be effective at killing pigmented TM cells without causing damage to adjacent, non-target cells, when used at short pulse durations, such as a nanosecond. The desired radiant exposure may be achieved by modifying the target spot size, the beam symmetry, or the delivered Joules/pulse. In general, the target spot size is large compared to those utilized in many previous applications of laser therapy to the eye; in preferred embodiments of the invention, the target spot size is from about 0.1 to about 1 mm in diameter. The large target spot size is possible because the method of the invention provides selective cell damage based on cell pigmentation, in contrast to prior art laser ablation methods, in which tissues are damaged nonselectively. For example, in prior techniques which ablate tissue by photodisruption, the high fluence which results in nonselective tissue ablation follows from the small target spot size, typically about 25 µm. It is a major advantage of the technique of the invention that focusing is not necessary to achieve selective killing; all cells within the irradiation field with chromophores which absorb the radiation will be affected. A large target area is advantageous: surgical time is minimized when the laser apparatus needs to be redirected fewer times. In a particularly preferred embodiment for treatment of the TM, the target area corresponds to or slightly exceeds the bounds of the TM, allowing irradiation of all of the cells within the TM.

Pulse durations of between about 1 nsec and about 2 µsec may be utilized. The desired pulse duration is related to the type and size of pigment particle within the target cells to be damaged. Since the thermal relaxation of a particle is related to the particle size of the pigment material, smaller intracellular particles require a shorter pulse duration to ensure confinement of energy to the target cells. Excessive pulse duration, such as more than five µsec or continuous waves, may cause nonselective killing of both pigmented and nonpigmented cells, as well as disruption of collagenous structures; this occurs as the longer laser exposure durations allow heat diffusion and resultant disruption of surrounding nontarget tissues. In contrast, prior art techniques employing ablation of tissue by coagulation utilize distinctly longer radiation durations.

More specifically, heat is confined within a spherical target for a thermal relaxation time, $T_r$, which is related to the target diameter, d, and the thermal diffusivity constant, D, by $T_r=d^2/4D$. During a lengthy laser exposure, greater than $T_r$, heat within the target diffuses to surrounding cells or structures resulting in coagulation. On the other hand, if heat is generated within the target more rapidly than heat can diffuse away, target temperatures become much higher than their surrounding tissues and thermal diffusion to surrounding structures is minimized. Thus, by choosing a pulse duration shorter than the thermal relaxation time of the target (i.e., melanin), selective target damage can be achieved. Assuming spherical targets of 0.5 to 5 microns, estimates of thermal relaxation times for biological targets range from $10^{-8}$ to $10^{-6}$ seconds. This is much shorter than the exposure time used in the prior art method of argon laser trabeculoplasty (ALT), where non-specific heating and coagulation of trabecular tissues results from the long exposure time (0.1 sec).

The emission wavelength of the laser may be within either the visible or infrared spectra, excluding the absorption lines of water. Additional selectivity for target cells may be provided by use of an appropriate laser wavelength. For example, when applying the method of the invention to retinal tissue, incidental absorption by hemoglobin in the retinal vessels may be avoided by selecting a wavelength of 1064 nm for ablating melanin-containing target cells; this wavelength is absorbed by melanin but not by hemoglobin. For avascular tissue, such as trabecular meshwork, a shorter wavelength of 532 nm provides higher absorption by melanin in pigmented cells and a shallower penetration depth into the tissue, as well as reducing the threshold energy for cell killing.

In a preferred mode of practicing the invention, a short-pulsed, Nd:YAG q-switched laser is used. Generally, Nd:YAG lasers emit at 1064 nm, and when frequency doubled yield 532 nm output. Both of these wavelengths are useful within the eye because they are transmitted by ocular media and structures including the cornea, aqueous humor, lens, vitreous and sclera.

There are several types of pigmented cells within the eye, which may be advantageously damaged with the method of the invention when clinically indicated. These cells acquire pigment by either synthesizing melanin endogenously or by phagocytosing exogenous pigment. Cell types which synthesize and retain melanin include the pigmented epithelial cells of the retina, ciliary body, and iris, as well as ocular melanomas. Although TM cells are incapable of synthesizing melanin, these cells typically acquire pigment by phagocytosis from the aqueous humor, which normally contains particles of pigmented cellular debris. In addition, the pigmentation of TM cells may be augmented by adding pigment to the aqueous humor, as is done in one preferred embodiment of the invention. This may be accomplished by injecting a suspension of pigmented particles into the anterior chamber of the eye with a fine needle. As the aqueous humor with suspended pigment particles flows from the eye through the TM, the TM cells take up pigment, increasing their optical density relative to surrounding nonpigmented tissue, and improving the cell selectivity of the laser killing of the invention. In a further preferred embodiment, melanin is introduced into the aqueous humor by laser iridotomy of the iris, which releases melanin particles from iris cells into the aqueous humor. Other pigments, such as india ink or any other nontoxic, insoluble particulate dye, may be introduced to phagocytic target cells prior to laser irradiation to ablate the pigmented cells.

In using the selective ablative method of the invention to treat glaucoma, the pigmented cells overlying the collagenous beams and plates of the TM are killed. While not intending to be bound or limited by a theory of why this method is beneficial in enhancing outflow of aqueous humor, the removal of established TM cells while preserving an intact collagenous meshwork allows repopulation of the meshwork by new, nonpigmented TM cells. While the pathophysiologic role of established TM cells in increased outflow resistance is unknown, the repopulated TM cells may better biologically cleanse the outflow pathway, and in other ways contribute to the maintainance of normal outflow resistance within the meshwork.

The method is useful for treating any disease where killing ocular pigmented cells is beneficial. The pigmented target cells may be on the surface of the cornea or conjunctiva, within the cornea or conjunctiva, or may constitute or be attached to any of the intraocular regions of the eye, such as the inner cornea, iris, ciliary body, lens, vitreous, choroid, retina, optic nerve, ocular blood vessels, or sclera, including any primary or metastatic tumors within or adjacent to these tissues. Specifically, diseases and conditions intended for treatment by this method include melanoma in any ocular tissue, diabetic retinopathy, and diseases of the retinal pigmented epithelium including drusen, macular edema, age-related macular degeneration, and central serous retinopathy, among others.

The term "patient" is meant to include any mammalian patient to which ocular laser therapy may be administered. Patients specifically intended for treatment with the method of the invention include humans, as well as nonhuman primates, sheep, horses, cattle, goats, pigs, dogs, cats, rabbits, guinea pigs, hamsters, gerbils, rats and mice.

Presently, there are a variety of commercially available laser systems for ophthalmic use, which may be adapted to perform the method of the invention. The commercially available ophthalmic surgical lasers can readily be modified, by anyone skilled in laser technology, to have the requisite enlarged target spot size, and hence low fluence, required by lasers useful in practicing the method of the invention.

An exemplary laser system used for practicing the present invention is shown in FIG. 1. As illustrated, the laser beam system consists of a power source 42 and an aiming beam source 54. The power source for the preferred mode of the invention is an Nd:YAG laser that is q-switched or q-switched ruby, with or without a frequency doubler. The system may include a lens 64 and detector 66 to monitor either wavelength or power emitted by the power source 42, a component of which is deflected off beam splitter 62. The aiming beam source 54 emits a beam which is deflected off mirror 56 to another splitter whereat one component is deflected through the remainder of the system, while another component passes through to a beam stop 60.

The power source beam 46 and the aiming beam 55 jointly pass through lens 49, within which they are focused to pass through a 100–600 micron optical fiber 50, having another mirror 51 therein. The guided beam 40 passes through lens 52 then is deflected by mirror 38. The energy 30 deflects off mirror 38 and into goniolens 34 where it is appropriately directed to the target tissue. After further deflecting off mirror 36, virtually parallel beams then reach the target cells at site 24 in the target eye 12.

The system may also include a viewing device 32, such as a camera or viewpiece, for viewing the aiming light for positioning and monitoring the target site 24. An auxiliary detector may be placed adjacent or proximal to the target site 24.

In an embodiment of the invention, laser irradiation is delivered through a slit-lamp delivery system such that an appropriate radiant exposure is achieved at the focal point of the slit-lamp optics.

Neutral density (ND) filters are used for attenuating the primary Nd:YAG laser beams. Helium-Neon laser is used for aiming purposes.

Melanin Phagocytosis by Trabecular Meshwork Cells:

All experiments were performed using third and fourth passage bovine TM cells grown in 6 or 24 well tissue culture plates in low glucose D-MEM with 10% fetal bovine serum, 1% penicillin-streptomycin, and 1% Fungizone (henceforth, media; Gibco, Buffalo, N.Y.) at 37 degree Celsius, 5% $CO_2$, and 95% humidity. TM cells are non-melanized in their normal growth state and serve as control non-melanized TM cells.

To obtain melanized TM cells, confluent TM cell cultures were challenged with sepia melanin in media at concentrations of $1 \times 10^6$ to $3 \times 10^7$ particles/ml and incubated for sixteen hours. Prior to incubation, melanin was washed three times with D-PBS (Gibco, $Ca^{2+}$, $Mg^{2+}$ free) and sonicated for 10 minutes to obtain a uniform suspension. Melanin concentration and size were determined using a Coulter Multisizer (Coulter Electronics, Hialeah, Fla.). The melanin incubation time was standardized to 16 hours. After sixteen hours, the cells were washed three times in D-PBS to remove the excess melanin and replaced with fresh media until irradiation. Just prior to irradiation, the media was replaced with D-PBS to avoid absorption of laser energy by the media. All irradiations occurred within four hours after excess melanin was removed.

As an additional control, TM cells were challenged with latex microspheres ($3 \times 10^7$ particles/ml, 0.9 μm in diameter, Polyscience, Warrington, Pa.) that contained no chromophore to determine the response of laser irradiation on TM cells with particulate material but without a chromophore. Following a 16 hr incubation, the TM cells were washed three times in D-PBS and irradiated with the laser systems described below.

In vitro monolayer cultures of bovine TM cells demonstrated avid phagocytosis of sepia melanin. Phase contrast photomicrographs of melanin uptake by TM cells at four different melanin concentrations (0, $3 \times 10^6 \times 10^7$ and $3 \times 10^7$ particles/ml) show that the distribution of melanin was perinuclear and the amount of melanin phagocytosed increased with high incubation concentrations. The incubation time of sixteen hours provided a qualitative difference in the amount of melanin ingested at these concentrations, which was used to differentiate the effects of TM cell pigmentation on the threshold energy for cell killing. Examination of TM cells challenged with latex microspheres also showed avid phagocytosis of latex microspheres with a perinuclear distribution of the microspheres.

Figure 2:
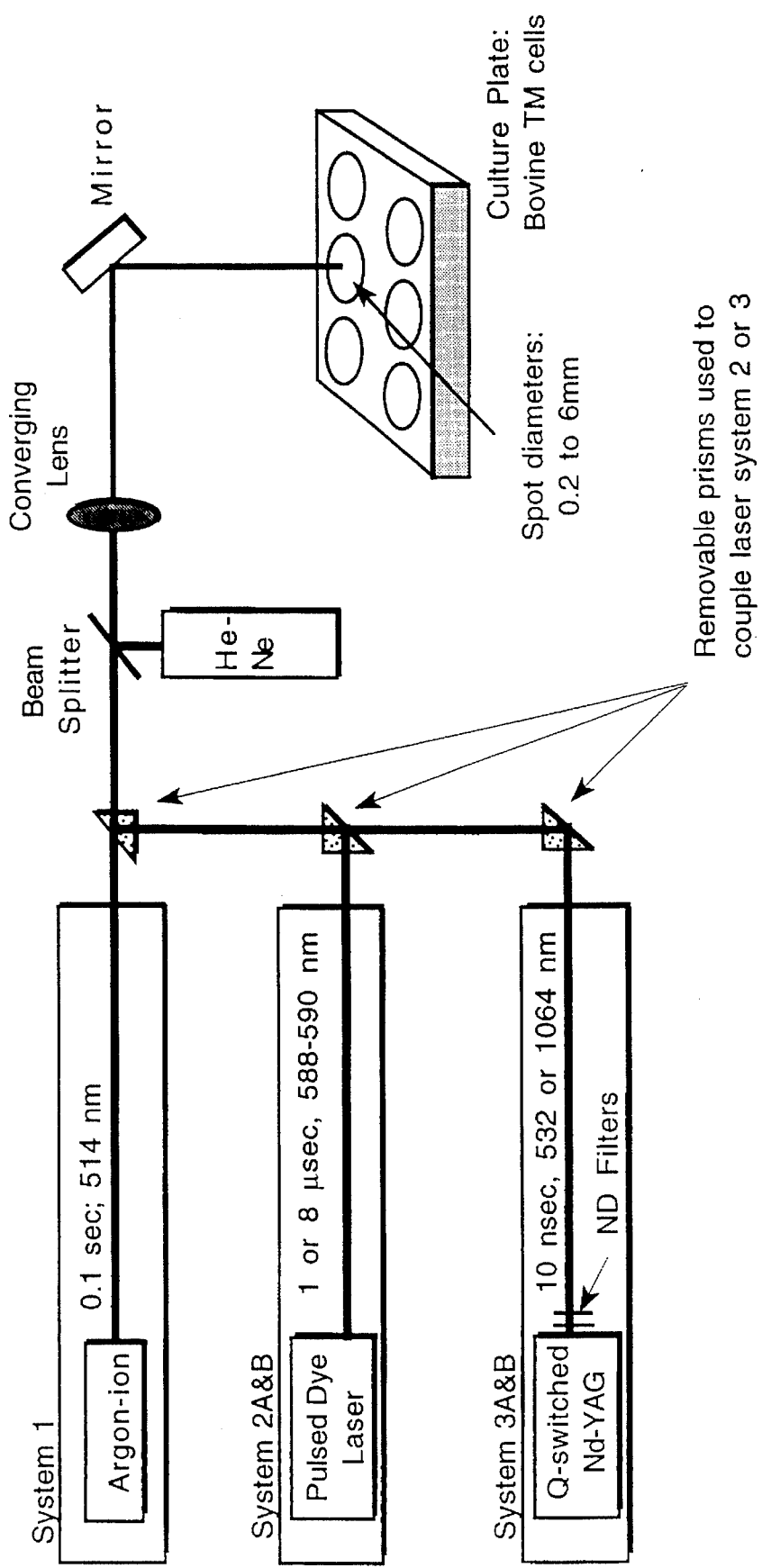
FIG. 2 is a diagram of the laser apparatus used in the in vitro experiments described below.

Laser Systems:

Irradiations of TM cells were performed using three laser systems. Each laser system had a different pulse duration. System-1 was a continuous wave argon-ion laser (Coherent Inc., Palo Alto, Calif. model #I100) emitting at 514 nm with a 0.1 second exposure time. System 2A was a flashlamp-pumped dye laser (Candela Laser Corp., Wayland, Mass.) emitting at 590 nm with pulse duration of 8 μsec. System 2B was a flashlamp-pumped dye laser (Candela Laser Corp., Wayland, Mass., model #SS500) emitting at 588 nm with pulse duration of 1 μsec. System-3A was a Q-switched frequency doubled Nd:YAG laser (Quantel International, Santa Clara, Calif. model #YG660A) emitting at 532 nm with a 10 nsec pulse duration. System-3B was a Q-switched normal mode Nd:YAG laser (Continuum Biomedical Inc., Livermore, Calif.) emitting at 1064 nm with a 10 nsec pulse duration. System-3B was used to determine wavelength dependency of the threshold response in the nanosecond pulse duration domain. The pulse energy was measured using an energy power meter (Scientech, Boulder, Colo., model #365) with ±10% accuracy. Threshold Response—Pulse Duration and Wavelength Dependence Studies TM cell cultures were irradiated at various radiant exposures using the experimental setup shown in FIG. 2. A Helium-Neon laser with an output of 3 mW, coupled into the optical path using a beam splitter, served as an aiming beam. A fiberoptic delivery was utilized for the argon-ion and pulsed-dye laser which resulted in a square (flat-top) pulse profile. The Nd:YAG lasers had a Gaussian profile. Spot diameters ranged from 0.2 to 6 mm. Each irradiation event consisted of a single pulse.

The threshold radiant exposure (mJ/cm$^2$) for cell killing was determined for TM cells with varying degree of melanization (melanin incubation concentration ranging from $1 \times 10^6$ to $3 \times 10^7$ particles/ml). The threshold radiant exposure for TM cell killing was defined as the minimum radiant exposure where cell cytotoxicity was observed using a fluorescent Live/Dead Viability/Cytoxicity assay (see below for detail, Molecular Probes Inc., Eugene, Oreg.). The threshold energy for SYSTEM-1 and SYSTEM-2 was measured by determining the ratio of dead cells/live cells within the irradiation zone. A micrometer equipped inverted fluorescent microscope (Carl Zeiss IM 35, Goettingen, Germany) was used to delineate the irradiation zone and count the number of dead cells vs. live cells. The Nd:YAG lasers (SYSTEM-3A&B) have a Gaussian beam profile which required a different method for determination of threshold energy, as described below.

Figure 3:
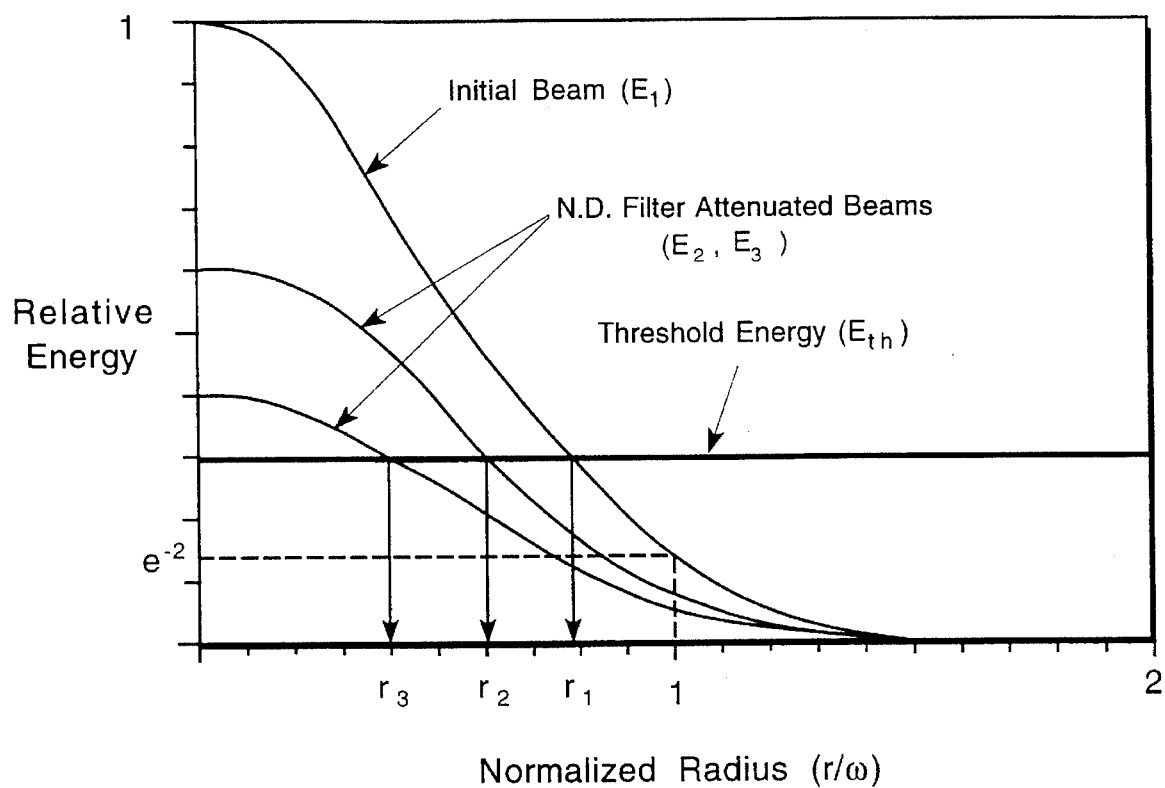
FIG. 3 is a graph depicting Gaussian profiles of three beam energies are depicted as $E_1$, $E_2$, and $E_3$, Irradiation of melanized trabecular meshwork cultures at these energies will result in a radius of cell killing of $r_1$, $r_2$, and $r_3$, respectively.

Method for Quantitation of the Threshold Energy for Cytotoxicity for the Nd: YAG Laser In contrast to laser System-1 and System-2, which have a uniform spatial energy distribution within the irradiation spot, the Nd:YAG laser emits a Gaussian beam with an energy distribution profile described by equation 1 and depicted in FIG. 3.

$$E(r)=E_t e^{-2(r^2/\omega^2)} \quad \text{(Equation 1)}$$

where:

$E(r)$=Pulse energy at a given radius, r.

$E_t$=Laser pulse energy.

r=Radius from center of beam.

ω=Constant, defined as Gaussian beam radius at $E(r)/E=1/e^2$

To determine the threshold energy for cell killing, $E_{th}$, we measure the radius of cell killing (by a fluorescent microscope with a reticule eye piece and the Live/Dead viability assay), $r_i$, at different energy levels $E_i$, where i=1, 2, 3, . . . , # of energy levels tested. At threshold energy level, $E_{th}$, we can substitute for $E(r)$ and r in equation 1 to obtain equation 2.

$$E_{th}=E_i e^{-2(r_i^2/\omega^2)} \quad \text{(Equation 2)}$$

where:

$E_{th}$=Threshold energy for cell killing.

$E_i$=Laser pulse energy.

$r_i$=Radius of cell killing at $E_i$.

Algebraic manipulation of equation 2 yields the following equation 3, which is in the form of y=mx+b.

$$2r_i^2=\omega^2 \ln[E_i]-\omega^2 \ln[E_{th}] \quad \text{(Equation 3)}$$

The linear form of equation 3 easily lends itself to an ordinary least square regression method. For example, in FIG. 3, Gaussian profiles of three beam energies are depicted as $E_1$, $E_2$, and $E_3$. Irradiation of melanized TM cultures at these energies will result in a radius of cell killing of $r_1$, $r_2$, and $r_3$, respectively. We can now determine threshold energy, $E_{th}$, by determining the best linear regression fit of the line defined by equation 3 (Estimated slope: m=ω$^2$. Estimated y-intercept: b=ω$^2$ln[$E_{th}$]). We can solve for threshold energy: $E_{th}=e^{(b/m)}/_{(\pi m)}$, where πm is the area of the laser beam at r=1/e$^2$.

Figure 4:
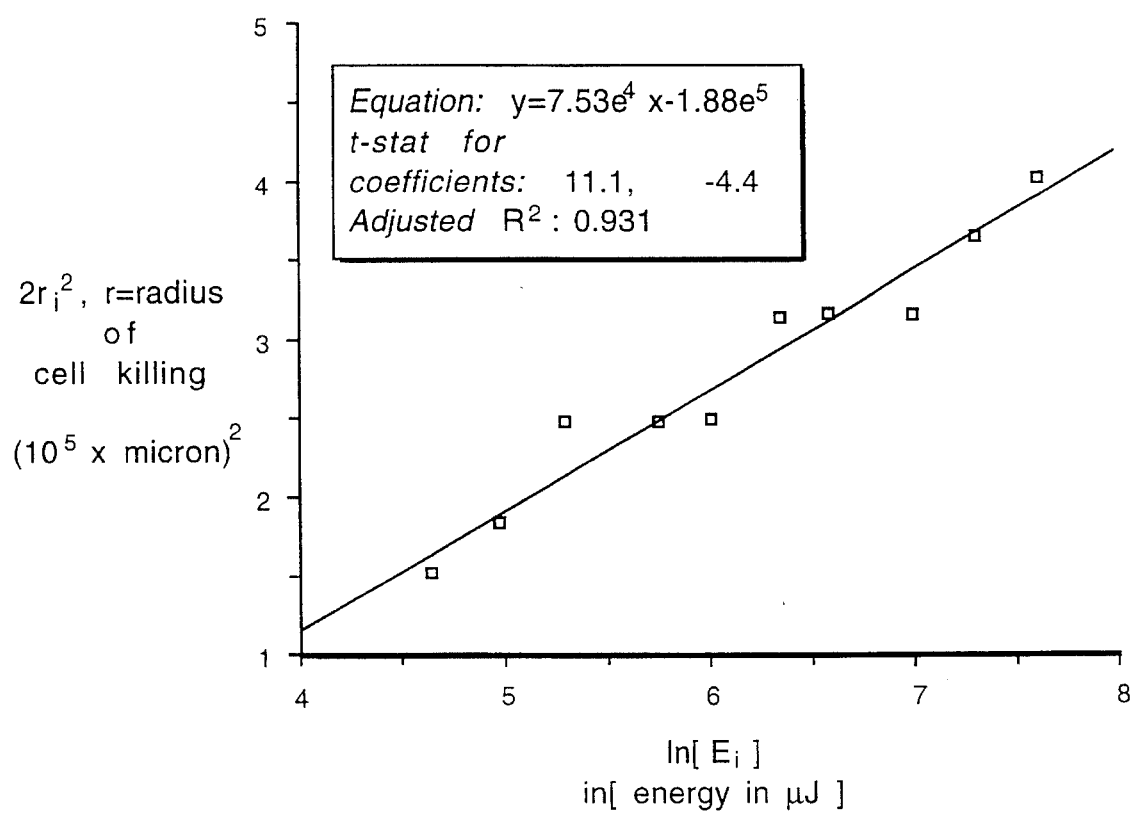
FIG. 4 is a graph of the threshold energy calculation for melanized trabecular meshwork cell (16 hours of $3\times10^7$ melanin/ml challenge) killing using a single pulse Nd:YAG laser. Estimated equations of the linear best fit and the significance of the coefficients are shown in the box.

For an actual threshold energy calculation, see FIG. 4, which depicts the threshold energy calculation for melanized TM cell (16 hours of $3 \times 10^7$ melanin/ml challenge) killing using a single pulse Nd:YAG laser. The estimated equation of the linear best fit and the significance of the coefficients are shown in the box. From the two estimated coefficients, the threshold energy for cell killing was calculated to be 12.2 μJ.

Threshold Energy for Cell Killing

The threshold energy for killing pigmented TM cells for the three laser systems is shown in Table 1.

TABLE 1

| THRESHOLD ENERGY FOR CELL KILLING | | |
|---|---|---|
| Melanin Concentration (million particles/ml) | Threshold Power (mW) | Threshold Radiant Exposure (mJ/cm$^2$) |
| System 1: CW Argon-ion Laser | | |
| 10 | 2100 | $6.7 \times 10^5$ |
| 15 | 1400 | $4.5 \times 10^5$ |
| 20 | 1000 | $3.2 \times 10^5$ |
| 30 | 750 | $2.4 \times 10^5$ |
| note: 514 nm emission; 0.1 sec pulse duration; 200 μm spot size. | | |
| System 2A: Pulsed Dye Laser | | |
| 1 | $6.3 \times 10^6$ | $1.6 \times 10^5$ |
| 5 | $3.9 \times 10^6$ | $1.0 \times 10^5$ |
| 10 | $2.2 \times 10^6$ | $5.7 \times 10^4$ |
| note: 590 nm emission; 8 μsec pulse duration; 200 μm spot size. | | |
| System 2B: Pulsed Dye Laser | | |
| 1 | $5.0 \times 10^8$ | $1.8 \times 10^3$ |
| 3 | $3.9 \times 10^8$ | $1.4 \times 10^3$ |

TABLE 1-continued

| | | |
|---|---|---|
| 10 | $2.3 \times 10^8$ | $8.1 \times 10^2$ |
| 30 | $1.6 \times 10^8$ | $5.8 \times 10^2$ | note: 588 nm emission; 1 μsec pulse duration; 6 mm spot size.
System 3A: Frequency Doubled Q-switched Nd:YAG Layer

| | | |
|---|---|---|
| 1 | $1.3 \times 10^8$ | 31 |
| 3 | $2.1 \times 10^8$ | 26 |
| 30 | $2.4 \times 10^8$ | 17 | note: 532 nm emission; 10 nsec pulse duration; 1 mm spot size.
System 3B: Normal mode Q-switched Nd:YAG Laser

| | | |
|---|---|---|
| 1 | $5.8 \times 10^9$ | $7.3 \times 10^3$ |
| 10 | $2.9 \times 10^9$ | $3.6 \times 10^3$ |
| 30 | $5.4 \times 10^8$ | $6.9 \times 10^2$ | note: 1064 nm emission; 10 nsec pulse duration; 1 mm spot size.

Figure 5:
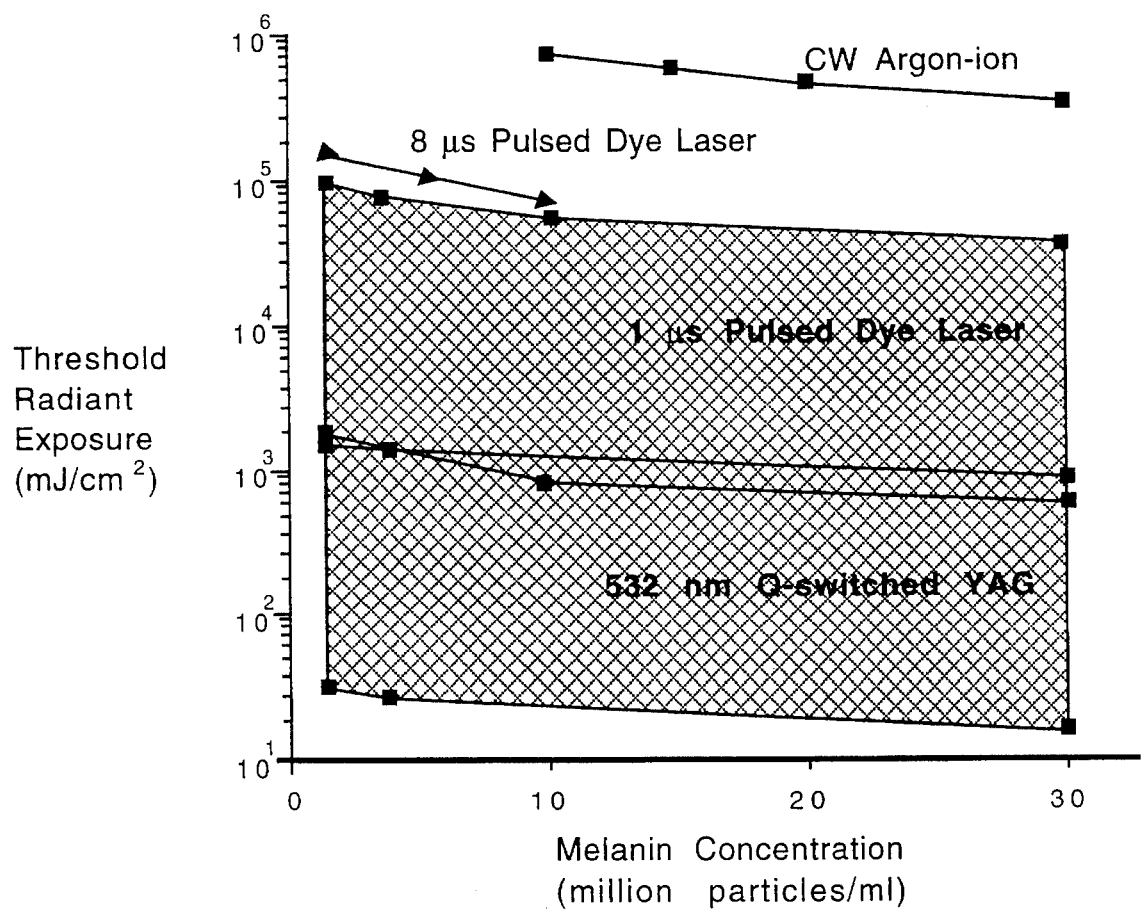
FIG. 5 is a graph of laser parameter ranges for in vitro selective cell killing.

FIG. 5 shows the threshold fluence for cell killing using the three laser systems following 16 hours incubation in $1 \times 10^6$ to $3 \times 10^7$ melanin particles/ml. Shaded regions indicate the combination of radiant exposure-melanin concentration parameters that will result in selective photothermolysis of the TM cells. Both the Pulsed Dye (588 nm, 1 μsec) laser and the Q-switched Nd:YAG (532 nm, 10 nsec) laser produce selective cell killing at threshold radiant exposure (base of the shaded region) and up to 20 times threshold energy. CW-Argon 514 nm, 0.1 sec pulse irradiations fail to produce selective cell-killing and this fact is depicted by a solid line. The graph shows that radiant exposure is an inverse function of the melanin concentration. Control irradiations of cells without melanin showed no evidence of cellular death with any of the laser systems using fluorescent cytotoxicity assay over a fluency range of $10-10^6$ mJ/cm$^2$. Similarly, irradiation of TM cells with latex microspheres resulted in no cellular death with any laser systems.

Figure 6:
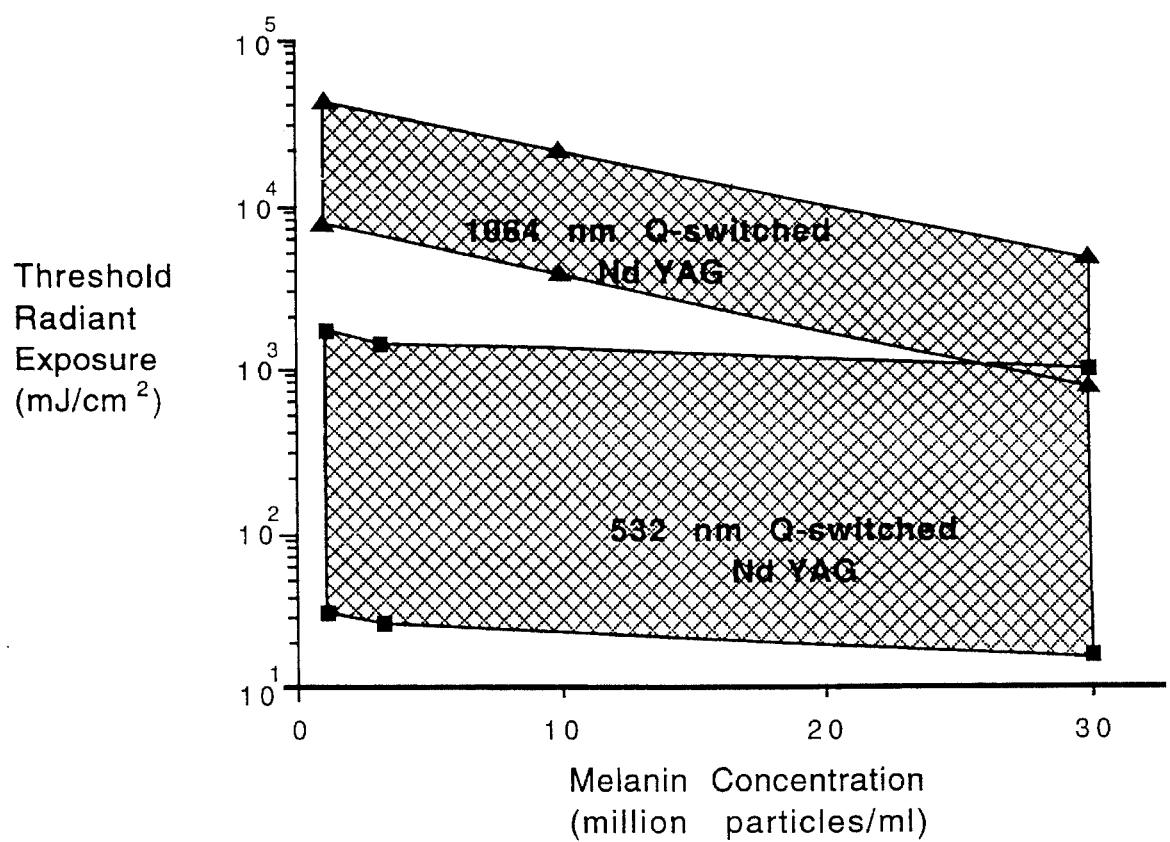
FIG. 6 is a graph of the wavelength dependence of laser parameter range for selective cell killing in vitro.

As expected from the decreased optical absorption by melanin at longer wavelengths, in comparing the two Nd:YAG lasers the threshold energy for cell killing increased with wavelength (see FIG. 6). Shaded regions represent the energy parameters that result in selective cell killing. At a melanin incubation concentration of $3 \times 10^7$ melanin particles/ml, the threshold energy for cell killing increases by a factor of 40, from 17 mJ/cm$^2$ to 690 mJ/cm$^2$, with an increase in wavelength from 532 nm to 1064 nm. The region of selective cell killing is also reduced from 20 times threshold energy to 4 times threshold energy when the wavelength is increased from 532 nm to 1064 nm. For all three lasers, the threshold energy for cell killing was inversely related to melanin concentration or the number of melanin particles within the cell.

A simple curve fit of a log(pulse duration) vs. log(threshold energy) plot suggests that at wavelengths between 514–588 nm, the threshold energy is proportional to the square root of the pulse duration ($E=8.4 \times 10^5 T^{0.52}$, where E-threshold energy, T=pulse duration; $R^2>0.99$). Consequently, reducing the pulse duration from 0.1 sec to 1 nsec (factor $10^8$) reduces the threshold energy by a factor of $10^4$. Selective Cell killing of Pigmented TM cells: Mixed non-melanized and melanized TM cell cultures Bovine TM cells were grown in two matching flasks (75 cm$^2$) to confluency as described above. One of the TM cell cultures was challenged with melanin ($3 \times 10^7$ particles/ml) for 16 hours and subsequently washed with D-PBS. The TM cell cultures (non-melanized and melanized) were then trypsinized (0.05% trypsin-0.2% EDTA, Gibco) for 10 minutes. The TM cell suspensions were recovered by centrifugation (1200 RPM for 15 min.) and resuspended in media. The two cell suspensions were combined and thoroughly mixed yielding a suspension of 1:1 mixture of non-melanized cells to melanized cells. The mixed cell suspension was immediately replated in 6 well or 24 well plates at confluent density, incubated for 6–24 hours to form a confluent culture and then irradiated.

The mixed confluent TM cell cultures (melanized and non-melanized TM cells were gently washed with D-PBS to remove excess cells and debris. The mixed cultures were then irradiated with each of the laser systems at radiant exposures ranging from subthreshold to suprathreshold to determine the range where selective killing of pigmented TM cells could be achieved. Within thirty minutes of irradiation, TM cell cytotoxicity/selectivity was determined using a Live/Dead Viability/Cytotoxicity Assay kit. The assay utilizes ethidium homodimer and calcein-AM, which respectively localizes to dead and live cells. Briefly, 200 to 300 μL of the assay solution (2.0 μM calcein-AM and 4.0 μM ethidium homodimer in D-PBS) was applied to each tissue culture well. The samples were incubated for 40 minutes at 37 degrees Celsius. Live and dead cells were differentiated by observation under an inverted fluorescent microscope with an ethidium bromide-fluorescein filter set. The cytoplasm of live cells stained green, while the nucleus of dead cells stained red. Using fluorescent and phase-contrast photomicrographs of the irradiated cell cultures. (Carl Zeiss IM 35, Goettingen, Germany), pigmented and non-pigmented TM cells within the same photographic fields were compared to determine selectivity for killing pigmented TM cells.

Using mixed melanized and non-melanized TM cell cultures, selectivity for killing only melanized TM cells was determined at various pulse durations and pulse energies. Selective killing of pigmented TM cells could not be achieved with pulse durations of 8 μsec or greater. Non-selective killing of both pigmented and adjacent non-pigmented TM cells within the irradiation field occurred using either the CW argon ion laser (system 1) emitting at 514 nm, with an exposure of 0.1 sec, or the Flash-lamp pulsed dye laser emitting at 590 nm with an 8 μsec pulse (system 2A), at threshold fluences. At fluences greater than threshold, many TM cells within the irradiation zone were completely vaporized.

However, selective killing of only melanized TM cells could be achieved using pulse durations of 1 μsec or less. Single cell selective cytotoxicity of melanized TM cells using the 1 μsec pulsed dye laser or the 10 nsec Q-switched Nd:YAG laser pulse was shown by TEM. Only those cells within the irradiation zone that contained melanin showed red nuclear staining using the fluorescent Live/Dead Assay. Adjacent non-melanized TM cells showed no evidence of cellular damage and showed green cytoplasmic staining. Damage to the TM cells containing pigment was so subtle that by phase contrast microscopy alone, without a fluorescent Live/Dead assay, it was difficult to morphologically differentiate the live from the dead cells. This indicates that selective killing of melanin containing TM cells can be achieved without gross disruption of the cellular architecture and without collateral damage to adjacent non-melanized TM cells.

The presence of particulate matter alone, without a chromophore, as demonstrated by irradiation of TM cells with latex microspheres, does not result in cell death.

The range of exposure dose (mJ/cm$^2$) in which selective killing of pigmented TM cells was maintained is also shown in FIGS. 5 and 6. Selectivity could be maintained with exposure doses approximately 20 times the threshold exposure dose with either the pulsed dye laser or the 532 nm Q-switched Nd:YAG laser. Selectivity could be maintained up to 4 times threshold exposure doses with the 1064 nm Q-switched Nd:YAG laser. At greater exposure doses, there was non-selective killing of TM cells and gross disruption or ablation of cells on the culture plate.

Transmission electron microscopy (TEM):

TEM was used to study the extent of cellular and/or intracellular damage and to verify the presence or lack of damage to adjacent non-melanized TM cells. Mixed cell cultures of melanized and non-melanized bovine TM cells and TM cell cultures of all melanized cells (melanin concentration $3\times10^6$) were plated at confluent density on round glass coverslips (Corning, Corning, N.Y.). Each set of cultures was irradiated with either the Q-switched Nd:YAG laser at a fluence of 120 mJ/cm$^2$ or with the microsecond pulsed-dye laser at 1 J/cm$^2$. A non-irradiated mixed cell culture was prepared as a control. Irradiated samples were fixed four hours after irradiation in 4% glutaraldehyde for one hour at room temperature. Cells were post-fixed in 0.5% osmium tetroxide in 0.1M sodium cacodylate buffer, pH 7.5, for 1 hour at room temperature. The cell monolayers on coverslips were processed through ethanol dehydration, infiltrated with increasing percentages of Epon 812:ethanol (Electron Microscopy Sciences, Fort Washington, Pa.), and embedded with inverted Beem capsules placed directly over the coverslips. The blocks were sectioned for TEM and the cells were examined with a transmission electron microscope (Model CM-10, Philips Corp., The Netherlands).

Cultures of non-mixed TM cells were evaluated prior to and four hours following irradiation with the nm Q-switched Nd:YAG laser, (10 nsec), and the 1 µsec pulsed dye laser. Electron photomicrographs demonstrated that ingested melanin is localized within lysosomes.

Following irradiation with a 10 nsec pulse from the Q-switched Nd:YAG laser (532 nm, 10 nsec pulse, 200 mJ/cm$^2$), melanin granules within the irradiated pigmented TM cells appear fractured and lysosomal membranes are ruptured. Adjacent mitochondria are not damaged, indicating that targeting is highly selective for melanin within lysosomes. Also, TEM of adjacent TM cells without melanin showed no evidence of ultrastructural damage.

TEM of melanized cells four hours after the cells had been irradiated with the pulsed dye laser (588 nm, 1 µsec pulse, 600 mJ/cm$^2$) demonstrated an amorphous appearance as if the melanin particles were melted with a loss of the surrounding lysosomal membranes. In contrast to TM cells irradiated with the Q-switched Nd:YAG laser, there was also evidence of thermal damage to the adjacent mitochondria with loss of the mitochondrial architecture, as shown in transmission electron micrographs. The nucleus showed no evidence of damage. Adjacent TM cells without melanin showed no evidence of ultrastructural damage.

Selective Laser Killing of TM In Vivo

In vivo application of the method of the invention was performed on owl monkeys with normal eyes. In the first group of animals, a pulsed dye laser was used, with a 1 µsec pulse duration. In another group of animals, the TM was treated with a 10 nsec pulse from a Q-switched Nd-YAG laser at a wavelength of 532 nm. In both groups, the laser used a slit lamp delivery system and a gonioscopic lens, and was aimed with a helium-neon beam. Each group of animals was treated with radiant exposure of 10 times threshold exposure.

After treatment, both groups of animals had a mild inflammatory reaction in the anterior chamber. Histological examination of trabecular meshwork tissue from the eyes of animals from both groups showed selective killing of pigmented trabecular meshwork cells.

It should be understood, however, that the foregoing description of the invention is intended merely to be illustrative by way of example only and that other modifications, embodiments, and equivalents may be apparent to those skilled in the art without departing from its spirit.

What is claimed is:

1. A method of selectively damaging pigmented intraocular cells in a patient with a disease, comprising:

selecting an intraocular area containing a pigmented cell and a nonpigmented cell, wherein the pigment is either endogenously synthesized or exogenous pigment synthesized by another intraocular cell, irradiating the area with laser radiation having a wavelength which is absorbed more in the pigmented cell than in the nonpigmented cell, wherein said radiation has a radiant exposure of between about 0.01 and about 5 Joules/cm$^2$, and damaging said pigmented cell without killing said nonpigmented cell.

2. The method of claim 1, wherein the radiation is delivered in pulses with pulse duration of between about 1 nsec and about 2 µsec.

3. The method of claim 1, wherein the radiation is delivered in a single pulse.

4. The method of claim 1, wherein the laser radiation impinges upon the intraocular area in a target spot of between about 0.05 and about 1.5 mm in diameter.

5. The method of claim 1, wherein the laser radiation impinges upon the intraocular area in a target spot of between about 0.1 and about 1 mm in diameter.

6. The method of claim 1, wherein the disease consists of glaucoma, melanoma, or a disease of the retinal pigmented epithelium.

7. The method of claim 1, wherein the intraocular area consists of trabecular meshwork, retina, ciliary body, iris, or an intraocular melanoma.

8. The method of claim 1, wherein the radiant exposure is between about 0.01 and about 1 Joules/cm$^2$.

9. The method of claim 1, wherein the pigmented cell consists of a trabecular meshwork cell, a retinal pigmented epithelial cell, a uveal pigmented cell, or a melanoma cell.

10. The method of claim 1, wherein said pigmented cell is a phagocytic cell within the intraocular area into which said pigment is introduced by contacting the phagocytic cell with the exogenous pigment before irradiating the area to damage the phagocytic cell.

11. The method of claim 10, wherein the phagocytic cell is a trabecular meshwork cell and the exogenous pigment contacts the phagocytic cell after being introduced into aqueous humor.

12. The method of claim 11, wherein the exogenous pigment is introduced into the aqueous humor by laser iridotomy of the iris.

13. The method of claim 1, wherein the intraocular area is trabecular meshwork, and wherein the laser radiation is delivered via a slit lamp delivery system and is directed into the trabecular meshwork by a goniolens.

14. A method of damaging trabecular meshwork cells, comprising:

selecting a region containing trabecular meshwork cells and collagen beams, wherein the trabecular meshwork cells contain pigment which is either endogenously synthesized or synthesized by another intraocular cell, irradiating the region of trabecular meshwork cells and collagen beams with laser radiation characterized by radiant exposure of between about 0.01 and about 5 Joules/cm² and a wavelength which is absorbed more in the trabecular meshwork cells than in the collagen beams, and damaging the trabecular meshwork cells without damaging the collagen beams.

15. The method of claim 14, wherein the radiation is delivered in pulses with pulse duration of between about 1 nsec and about 2 μsec.

16. The method of claim 14, wherein the radiation is delivered in a single pulse.

17. The method of claim 14, wherein the laser radiation impinges upon the intraocular area in a target spot of between about 0.05 and about 1.5 mm in diameter.

18. The method of claim 14, wherein the laser radiation impinges upon the intraocular area in a target spot of between about 0.1 and about 1 mm in diameter.

19. The method of claim 14, wherein the radiant exposure is between about 0.01 and about 1 Joules/cm².

20. The method of claim 14, further comprising the step of introducing exogenous pigment into a phagocytic cell within the region of trabecular meshwork by contacting the phagocytic cell with exogenous pigment before irradiating the region to damage the trabecular meshwork cells.

21. The method of claim 20, wherein the phagocytic cell is a trabecular meshwork cell and the exogenous pigment contacts the phagocytic cell after being introduced into aqueous humor.

22. The method of claim 21, wherein the exogenous pigment is introduced into the aqueous humor by laser iridotomy of the iris.

23. A method of damaging conjunctival pigmented epithelial cells in a patient with a disease, comprising:

selecting an area of conjunctiva containing pigmented cells and nonpigmented cells, wherein the pigment is either endogenously synthesized or exogenous pigment synthesized by another intraocular cell, irradiating the area with radiation, wherein said radiation has radiant exposure of between about 0.01 and about 5 Joules/cm² and has a wavelength which is absorbed more in the pigmented cells than in the nonpigmented cells, and damaging said pigmented cells without killing said nonpigmented cells.

24. The method of claim 23, wherein the radiation is delivered in pulses with pulse duration of between about 1 nsec and about 2 μsec.

25. The method of claim 23, wherein the laser radiation has a wavelength which is more highly absorbed in pigmented than in nonpigmented cells.

26. The method of claim 23, wherein the disease consists of conjunctival melanoma or pigmented nevus.

27. A method of selectively damaging a pigmented phagocytic cell in a patient with a disease, comprising:

selecting an intraocular area containing said phagocytic cell and a nonpigmented cell, introducing exogenous pigment into said phagocytic cell by contacting said cell with exogenous pigment introduced into the aqueous humor of said patient by laser iridotomy of the iris of said patient, irradiating the intraocular area with laser radiation having a radiant exposure of between about 0.01 and about 5 Joules/cm², and damaging said phagocytic cell without killing said nonpigmented cell.

28. A method of selectively damaging a pigmented trabecular meshwork cell in a patient with a disease, comprising:

selecting an intraocular area containing said trabecular meshwork cell and a nonpigmented cell, introducing exogenous pigment into said trabecular meshwork cell by contacting said cell with exogenous pigment introduced into the aqueous humor of said patient by laser iridotomy of the iris of said patient, irradiating the intraocular area with laser radiation having a radiant exposure of between about 0.01 and about 5 Joules/cm², and damaging said trabecular meshwork cell without killing said nonpigmented cell.

29. A method of treating glaucoma in a patient, said method lowering an intraocular pressure in the patient by selectively damaging pigmented intraocular cells, said method comprising:

selecting an intraocular area containing a pigmented cell and a nonpigmented cell, wherein said pigment is either endogenously synthesized or exogenous pigment synthesized by another intraocular cell, irradiating the intraocular area with laser radiation having a wavelength which is absorbed more in said pigmented cell than in said nonpigmented cell, wherein said radiation has a radiant exposure of between about 0.01 and about 5 Joules/cm², and damaging said pigmented cell without killing said nonpigmented cell to lower the intraocular pressure in the patient.

* * * * *